US010070859B1

(12) United States Patent
Nason

(10) Patent No.: US 10,070,859 B1
(45) Date of Patent: Sep. 11, 2018

(54) SYSTEMS AND METHODS FOR PASSING A RACKING HITCH THROUGH TISSUE

(71) Applicant: Cayenne Medical, Inc., Scottsdale, AZ (US)

(72) Inventor: Kevin S. Nason, Chandler, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 294 days.

(21) Appl. No.: 14/757,710

(22) Filed: Dec. 22, 2015

Related U.S. Application Data

(60) Provisional application No. 62/095,720, filed on Dec. 22, 2014.

(51) Int. Cl.
*A61B 17/04* (2006.01)
*A61M 29/00* (2006.01)
*A61B 17/06* (2006.01)

(52) U.S. Cl.
CPC ...... *A61B 17/0491* (2013.01); *A61B 17/0469* (2013.01); *A61B 17/06166* (2013.01)

(58) Field of Classification Search
CPC ......... A61M 29/00; A61B 2017/00663; A61B 2017/0609; A61B 2017/06052; A61B 2017/06009; A61B 2017/047; A61B 2017/0472; A61B 17/04; A61B 17/0469; A61B 17/0482; A61B 17/0483; A61B 17/0057
See application file for complete search history.

(56) References Cited

U.S. PATENT DOCUMENTS

| 4,957,498 A | * | 9/1990 | Caspari | .............. | A61B 17/0469 606/144 |
| 6,443,963 B1 | * | 9/2002 | Baldwin | ............ | A61B 17/0482 606/139 |

* cited by examiner

*Primary Examiner* — Victor Nguyen
(74) *Attorney, Agent, or Firm* — Schwegman Lundberg & Woessner, P.A.

(57) ABSTRACT

A suture loop is used in combination with a grasp-and-retrieve suture passer to pass a racking hitch through tissue in one step.

19 Claims, 3 Drawing Sheets

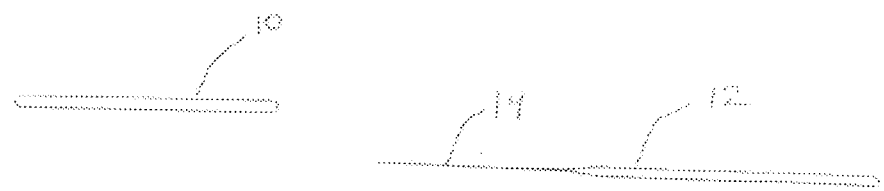
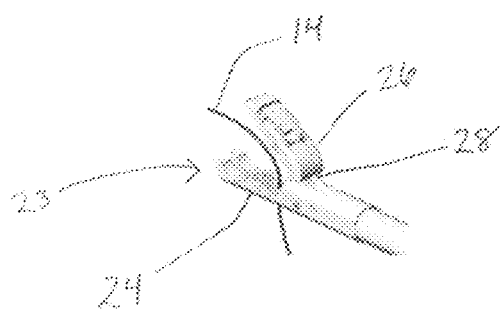
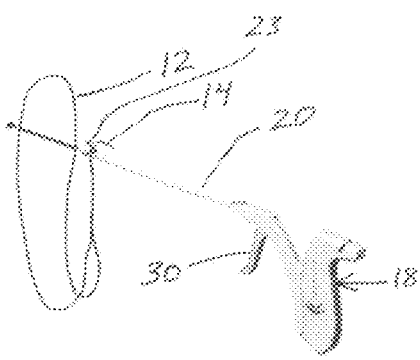
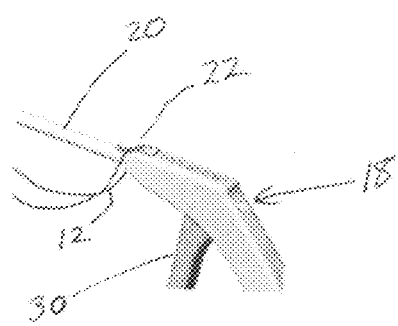

SYSTEMS AND METHODS FOR PASSING A RACKING HITCH THROUGH TISSUE

This application claims the benefit under 35 U.S.C. 119(e) of the filing date of Provisional U.S. Application Ser. No. 62/095,720, entitled System and Method for Passing a Racking Hitch Through Tissue, filed on Dec. 22, 2014, which application is expressly incorporated herein by reference, in its entirety.

BACKGROUND OF THE INVENTION

In recent years, rotator cuff suture passers have become commonly used during arthroscopic surgical procedures. For many types of repairs, the surgeon needs to arthroscopically pass sutures—often many—through soft tissues that have become detached from bone. These passers have made it quick and easy to pass suture through tissue. However, large repairs can often require many suture passes, especially if a secure hold on the tissue is required, leading to difficult suture management issues.

As noted above, there are currently many suture passers on the market designed to pass suture through soft tissue. These passers typically comprise an articulating jaw on the end of a shaft that can be passed through a cannula (if used in an arthroscopic procedure) and used to grasp tissue where the suture is going to be passed. The surgeon squeezes the handle to advance a flexible suture needle (with the suture attached) from the bottom jaw, up through the tissue, and through the top jaw. When the needle is retracted, a loop of suture is left on the top of the tissue. This loop can be retrieved using a suture grasper, leaving a simple stitch through the tissue. More recently, "grasp-and-retrieve" suture passer designs have been developed. These passers have a trap door or other suture catching mechanism in the top jaw. When the suture needle and suture are passed up through the tissue and the passer top jaw, the loop is captured by this catching mechanism. When the suture passer is pulled out of the cannula and joint space, the suture end loop is pulled out with it, eliminating the step of retrieving the suture loop with the grasper. This feature can be very useful in areas of poor visibility or if the surgeon does not have a hand available (because one is holding the arthroscope and the other is holding the suture passer). The passed suture can then be loaded into a knotless suture anchor, passed through additional tissue, or tied to other sutures to approximate and secure tissue to bone.

The current tools work well to pass a simple stitch through flat tissue, such as the rotator cuff tendons. However, a simple stitch through tissue is not as secure as other types of stitches, such as a mattress or Mason-Allen stitch. Also, as the sutures are passed through the tissue multiple times to create more secure stitches, suture management can become difficult, requiring a high degree of surgeon skill or increasing the duration of the procedure.

SUMMARY OF THE INVENTION

The following disclosure describes a method for using a suture loop in combination with a grasp-and-retrieve suture passer to pass a racking hitch through tissue in one step.

More particularly, in one aspect of the invention there is disclosed a system for passing a racking hitch through tissue, which comprises a suture passer comprising a handle, a shaft extending distally from the handle, and first and second clamping jaws extending distally from the shaft, wherein the second clamping jaw is movable relative to the first clamping jaw between a closed orientation and an open orientation. The handle includes an actuator for moving the first and second clamping jaws between the open and closed orientations. A spring clip is disposed on a distal end of the handle. A length of suture is loaded into one of the first and second clamping jaws. The spring clip is adapted to secure a portion of the length of suture during a procedure for creating the racking hitch. In one embodiment, the length of suture comprises a continuous loop of suture. In other, currently preferred embodiments, the length of suture comprises a single strand tail of suture connected to a loop of suture.

The spring clip preferably comprises a leaf spring.

In another aspect of the invention, there is disclosed a method of creating a racking hitch suture stitch through a portion of tissue, which comprises a step of loading a suture loop into a jaw of a clamping mechanism of a suture passer, wherein the clamping mechanism comprises a pair of jaws relatively movable with respect to one another between a closed clamping position and an open position. A shaft of the suture passer is passed through the suture loop, following which a portion of the suture loop is secured to a suture spring clip. The clamping mechanism is positioned, in its open configuration around tissue through with the suture loop is to be passed, at a procedural site. The clamping mechanism is closed to pass the suture loop through the tissue. Following this step, the suture passer is withdrawn proximally out of the procedural site, thereby releasing the suture loop from the suture spring clip so that the released portion of the suture loop slides distally down the suture passer shaft and tightens in a racking hitch around the tissue.

The invention, together with additional features and advantages thereof, may be best understood by reference to the following description taken in conjunction with the accompanying illustrative drawings. In these accompanying drawings, like reference numerals designate like parts throughout the figures.

BRIEF DESCRIPTION OF THE DRAWINGS

FIG. 1 is a schematic view of a continuous suture loop which may be used in the inventive system and method;

FIG. 2 is a schematic view of a suture loop with a single strand tail which may alternatively be used in the inventive system and method;

FIG. 3 is an isometric view of a distal end of a suture passer for use with the inventive system and method;

FIG. 4 is an isometric view illustrating a suture passer for use with the inventive system and method wherein the passer shaft is passed through a suture loop;

FIG. 5 is an isometric view illustrating the suture loop secured in a suture spring clip provided on the suture passer of the invention;

DETAILED DESCRIPTION OF THE INVENTION

Referring now more particularly to the drawings, the present invention utilizes a suture loop, which may comprise a continuous suture loop 10, as shown in FIG. 1, or a suture loop 12 with a single strand tail 14, as shown in FIG. 2.

The suture loop 10 of FIG. 1, known in the prior art, is constructed such that there is a thicker section where the two ends of the suture length forming the loop are woven together. This thicker section may be loaded, by chance, into a suture passer or knotless anchor and be stuck or degrade the anchor performance. For this reason, the inventive suture loop 12 with single strand tail 14 is preferred for use in the present invention. In this FIG. 2 embodiment, the tail 14 provides a designated, single strand section to load into the suture passer.

Figure 6:
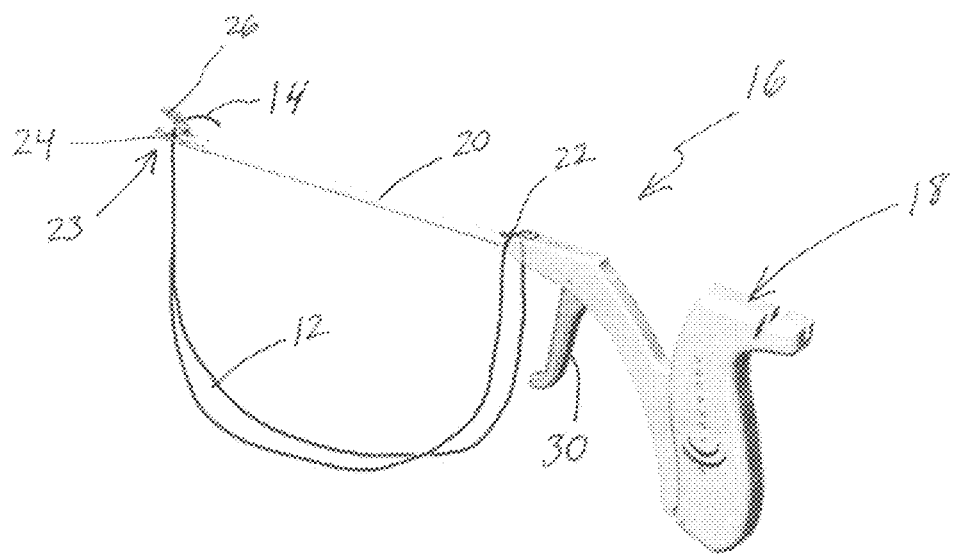
FIG. 6 is an isometric view of a suture passer according to the invention which has been loaded with suture loop.

As shown most particularly in FIGS. 4 and 6, a suture passer 16 comprises a handle 18 and a shaft 20. A suture spring clip 22 is disposed on a distal end of the handle 18, in such a manner that a proximal end of the suture spring clip 22 is attached to the handle 18, and a distal end of the suture spring clip 22 extends from the mounted proximal end of the spring clip and along a portion of each of the distal end of the handle and a proximal end of the shaft 20. The suture spring clip 22 is formed of a suitable resilient material so that the distal end of the suture spring clip is adapted for clamping a portion of suture between the spring clip and the handle or shaft. Its purpose is to secure the loop end 12 of the suture over the shaft 20 of the suture passer 16, as will be described more fully below.

At a distal end of the shaft 20 is a grasping jaw system 23 comprising a passer jaw 24 and a top jaw 26, as shown in FIGS. 3, 4, and 6. The top jaw 26 is movable relative to the passer jaw 24 about a transverse pivot axis 28 between a closed orientation, wherein the top jaw 26 is clamped down and engaged with the passer jaw 24, and an open orientation, as shown in FIGS. 3, 4, and 6. A trigger 30, disposed on the handle 18, actuates the top jaw 26 between its open and closed orientations.

To perform the inventive method, the suture loop 12 is loaded into the suture passer 16 by loading the tail 14 (or a portion of the continuous loop 10 if such an embodiment is selected) into and through an aperture of the passer jaw 24, as shown in FIG. 3. Then, as shown in FIG. 4, the suture passer shaft 20 is passed through the suture loop 12 (or 10). As illustrated in FIG. 5, a portion of the suture loop 12 is then secured by the suture spring clip 22.

FIG. 6 illustrates the loaded configuration of the inventive suture passing device 16 described above.

Figure 7:
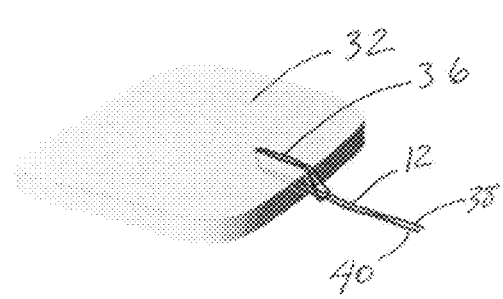
FIGS. 7 and 8 are isometric views illustrating a racking hitch stitch through tissue.
Figure 8:
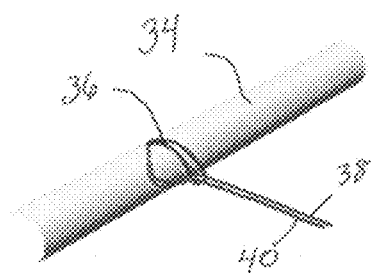

To create a racking hitch stitch through tissue 32 (FIG. 7) or around tissue 34 (FIG. 8), the practitioner positions the jaws 24, 26, in their open configuration, around the tissue 32, 34 through which the suture 12 is to be passed. The suture 12 is passed up through the tissue by action of the closing of the jaws 24, 26 to their closed orientation, using the trigger 30 and one or more needles disposed within the jaws 24, 26, whereby the suture is captured in the top jaw 26. When the suture passer 16 is pulled out of the joint space and cannula, used for access to the procedural site, the suture 12 releases from the suture spring clip 22, slides down the suture passer shaft 20, and tightens in a racking hitch 36 around the tissue. The resulting stitch is shown in FIGS. 7 and 8.

This racking hitch stitch 36 through the tissue 32, 34 provides a secure hold on the tissue that tightens as tension is applied. The suture tail can be used or cut off to leave two free ends of suture 38, 40. The two free ends 38, 40 can then be separated and loaded into two different anchors in different locations if desired. The tail or tails can be used in many configurations to complete a range of procedures. These procedures may comprise, for example, loading one or both tails 38, 40 into a knotless anchor to approximate and secure tissue to bone, passing them through a transosseous tunnel to approximate and secure tissue to bone, passing the suture free ends through additional soft tissues to approximate and secure the tissues together, using the suture free ends to tag tissue or tendon for further steps (e.g. externalizing and trimming a biceps tendon or passing through an ACL graft to manipulate for whipstitching, or using the suture free ends in place of whipstitching on an ACL graft or biceps tendon, or the like.

Figure 9:
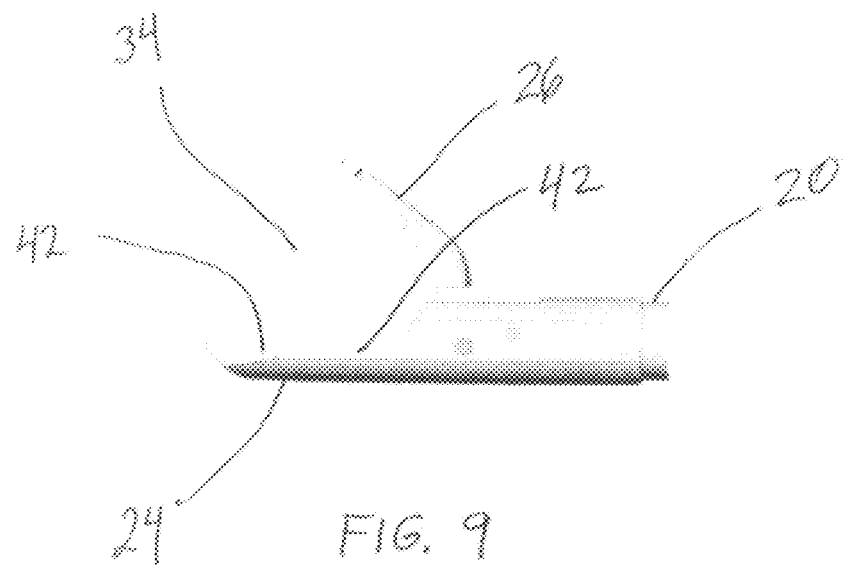
FIGS. 9 and 10 illustrate an alternative embodiment of a jaw design for use with the suture passer of the invention, for particular use with tendons or the like having a round configuration.
Figure 10:
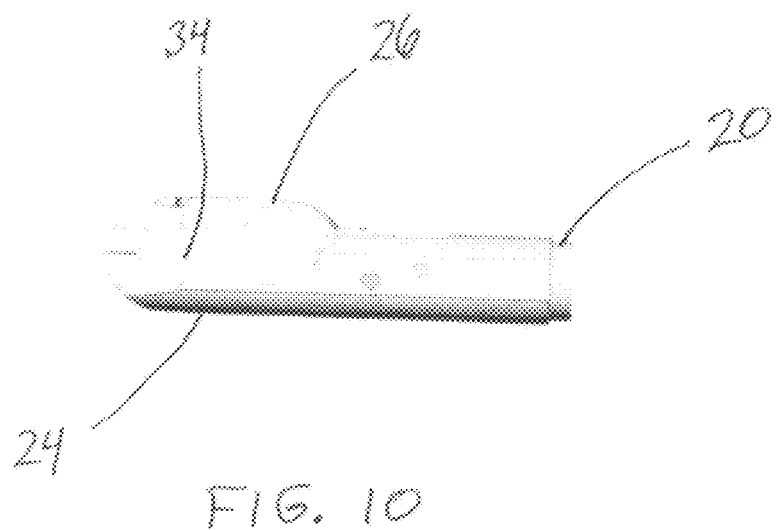

There are other design enhancements that can be incorporated into the inventive system to make the procedure simpler for specific tissue repairs. For example, the jaws of the suture passer can be modified for grasping and passing suture through specific tissues, such as round tendons, such as the biceps tendon, or capsule tissue in the labrum. An example of a modified suture passer jaw design for passing a racking hitch through the biceps tendon is shown in FIGS. 9 and 10.

The jaws 24, 26 of the grasper are shaped to pass around and squeeze a round tendon, specifically by the incorporation of recesses 42 in the passer jaw 24. The path of the needle through the tissue is designed such that the resulting stitch passes beyond the center of the round tendon cross-section, resulting in a very strong stitch through tendon.

The suture spring clip 22 holds the suture loop in place and aids with suture management during the procedure. The procedure can be followed to form the racking hitch without the suture spring clip, as long as the passer shaft is passed through the suture loop prior to passing suture through the tissue.

In a presently preferred embodiment, the suture spring clip 22 comprises a simple leaf-spring design. The function of the clip is to hold the suture loop in place on top of the passer shaft during passing, and then to release the loop without user intervention as it is pulled down around the tissue. The design is simple and allows the suture to be loaded into and removed from the clip easily.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:
1. A method of creating a racking hitch suture stitch through a portion of tissue, comprising:
   loading a suture loop into a jaw of a clamping mechanism of a suture passer, wherein the clamping mechanism comprises a pair of jaws relatively movable with respect to one another between a closed clamping position and an open position;
   passing a shaft of the suture passer through the suture loop;
   securing a portion of the suture loop using a suture spring clip;
   positioning the clamping mechanism, in its open position around tissue through which the suture loop is to be passed, at a procedural site;
   closing the clamping mechanism to pass the suture loop through the tissue; and
   pulling the suture passer proximally out of the procedural site, thereby releasing the suture loop from the suture spring clip so that the released portion of the suture loop slides distally down the suture passer shaft and tightens in a racking hitch around the tissue.

2. The method of claim 1, wherein closing the clamping mechanism comprises manipulating an actuator operable for moving the pair of jaws between the open and closed positions.

3. The method of claim 2, wherein the actuator is a trigger that extends from a handle of the suture passer.

4. The method of claim 1, wherein the suture loop comprises a continuous loop of suture.

5. The method of claim 1, wherein the suture loop comprises a single strand tail of suture connected to a loop of suture.

6. The method of claim 5, wherein loading the suture loop into the jaw of the clamping mechanism comprises loading the tail into a passer jaw of the pair of jaws.

7. The method of claim 6, wherein the tail of the suture loop is inserted through an aperture of the passer jaw.

8. The method of claim 6, further comprising cutting the tail, after pulling the suture passer proximally out of the procedural site, to provide two free ends of suture.

9. The method of claim 8, further comprising loading the two free ends of suture into two different anchors.

10. The method of claim 8, further comprising loading one or both of the two free ends of suture into a knotless anchor.

11. The method of claim 1, wherein the pair of jaws comprises a passer jaw and a top jaw, the top jaw movable relative to the passer jaw about a transverse pivot axis between the closed position and the open position.

12. The method of claim 1, wherein the racking hitch provides a secure hold on the tissue that tightens as tension is applied.

13. The method of claim 1, wherein the suture spring clip comprises a leaf spring.

14. A method of creating a racking hitch suture stitch through a portion of tissue, comprising:
  loading a suture loop into a first jaw of a clamping mechanism of a suture passer, wherein the clamping mechanism comprises the first jaw and a second jaw relatively movable with respect to the first jaw between a closed clamping position and an open position;
  passing a shaft of the suture passer through the suture loop;
  positioning the clamping mechanism, in its open position around tissue through which the suture loop is to be passed, at a procedural site;
  closing the clamping mechanism to pass the suture loop through the tissue; and
  pulling the suture passer proximally out of the procedural site, thereby releasing the suture loop from a suture spring clip so that the released portion of the suture loop slides distally down the suture passer shaft and tightens in a racking hitch around or through the tissue.

15. The method of claim 14, wherein the suture loop comprises a continuous loop of suture.

16. The method of claim 14, wherein the suture loop comprises a single strand tail of suture connected to a loop of suture.

17. The method of claim 16, wherein loading the suture loop into the first jaw of the clamping mechanism comprises loading the tail into the first jaw.

18. The method of claim 17, wherein the tail of the suture loop is inserted through an aperture of the first jaw.

19. The method of claim 14, wherein the suture spring clip comprises a leaf spring.

\* \* \* \* \*